(12) United States Patent
Tokarski et al.

(10) Patent No.: US 7,244,541 B2
(45) Date of Patent: *Jul. 17, 2007

(54) LINKED DIHYDRAZONE-BASED CHARGE TRANSPORT COMPOUNDS

(75) Inventors: Zbigniew Tokarski, Woodbury, MN (US); Nusrallah Jubran, St. Paul, MN (US); Vytautas Getautis, Kaunas (LT); Edmundas Montrimas, Vilnius (LT); Maryte Daskeviciene, Jonava (LT); Valentas Gaidelis, Vilnius (LT); Vygintas Jankauskas, Vilnius (LT)

(73) Assignee: Samsung Electronics Co., Ltd., Suwon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 11/274,942

(22) Filed: Nov. 15, 2005

(65) Prior Publication Data

US 2006/0127794 A1 Jun. 15, 2006

Related U.S. Application Data

(62) Division of application No. 10/431,138, filed on May 7, 2003, now Pat. No. 6,964,833.

(60) Provisional application No. 60/385,249, filed on May 31, 2002.

(51) Int. Cl.
G03G 13/10 (2006.01)

(52) U.S. Cl. .......................................... 430/117; 430/73

(58) Field of Classification Search ............. 430/58.45, 430/58.6, 72, 73, 78, 79, 56, 117, 58, 45
See application file for complete search history.

(56) References Cited

U.S. PATENT DOCUMENTS

| | | | |
|---|---|---|---|
| 4,297,426 A | 10/1981 | Sakai et al. |
| 4,476,137 A | 10/1984 | Haviv et al. |
| 4,786,571 A | 11/1988 | Ueda |
| 4,957,838 A | 9/1990 | Aruga et al. |
| 5,128,227 A | 7/1992 | Monbaliu et al. |
| 5,174,116 A | 12/1992 | Ishikawa |
| 5,737,669 A | 4/1998 | Ring |
| 5,932,384 A | 8/1999 | Mitsumori et al. |
| 6,001,522 A | 12/1999 | Woo et al. |
| 6,020,096 A | 2/2000 | Fuller et al. |
| 6,030,734 A | 2/2000 | Mitsumori |
| 6,066,426 A | 5/2000 | Mott et al. |
| 6,099,996 A | 8/2000 | Yanus et al. |
| 6,140,004 A | 10/2000 | Mott et al. |
| 6,214,503 B1 | 4/2001 | Gaidelis et al. |
| 6,340,548 B1 | 1/2002 | Jubran et al. |
| 6,670,085 B2 | 12/2003 | Jubran et al. |
| 6,689,523 B2 | 2/2004 | Law et al. |
| 6,696,209 B2 | 2/2004 | Law et al. |
| 6,749,978 B2 | 6/2004 | Jubran et al. |
| 6,905,804 B2 | 6/2005 | Law et al. |
| 7,118,839 B2 | 10/2006 | Law et al. |
| 2003/0104294 A1 | 6/2003 | Law et al. |
| 2003/0113132 A1 | 6/2003 | Law et al. |
| 2005/0095518 A1* | 5/2005 | Grazulevicius et al. ....... 430/73 |

FOREIGN PATENT DOCUMENTS

| | | |
|---|---|---|
| GB | 1047525 | 11/1966 |
| JP | 62116943 | 5/1987 |

OTHER PUBLICATIONS

Diamond, Arthur S., ed. *Handbook of Imaging Materials*, Marcel Dekker, Inc. NY (1991), pp. 380-382, 395-396.
Atherton et al., *Synthesis of 3(S)-Acylamino-1-[(Phenyl)(1H-Tetrazol-5-YL)Amino]-2-Azetidinones*, Symposia-in-Part No. 10: Recent Aspects of the Chemistry of β-Lactams, 1983, vol. 39, No. 15., pp. 2599-2608.
Murakami et al., *An Efficient Synthesis of 1,1-Disubstituted Hydrazines*, Chemical & Pharmaceutical Bulletin, Feb. 1983, vol. 31, No. 2, pp. 423-428.
Boyd et al., *The Dimerisation of 5-Methylene-Δ²-1,3,4-oxadiazolines*, Journal of The Chemical Society, 1971, pp. 2314-2317.

\* cited by examiner

*Primary Examiner*—Janis L. Dote
(74) *Attorney, Agent, or Firm*—Patterson Thuente Skaar & Christensen, P.A.

(57) ABSTRACT

Improved organophotoreceptors comprise:
(a) a charge transport compound having the formula

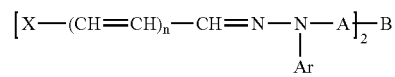

where n is an integer from 0 to 1;
X is an (N,N-disubstituted)arylamine group;
Ar is an aryl group or a heterocyclic group;
A is a first linking group with the formula $-(CH_2)_p-$ which can be branched or linear, where p is an integer from 3 to 20 inclusive; and
B is a second linking group having the formula -Q-Z-Q', where Q and Q' are, independently, O, S, or $NR_1$; wherein when Q or Q' is $NR_1$ or Q=O and Q'=S, Z comprises an aryl group, and wherein when Q=Q'S or Q=Q'=O, Z comprises a multi-ring conjugated group;
(b) a charge generating compound; and
(c) an electrically conductive substrate over which said charge transport compound and said charge generating compound are located.

3 Claims, 2 Drawing Sheets

LINKED DIHYDRAZONE-BASED CHARGE TRANSPORT COMPOUNDS

CROSS REFERENCE TO RELATED APPLICATIONS

This application is a divisional application of U.S. patent application Ser. No. 10/431,138 filed on May 7, 2003 (now U.S. Pat. No. 6,964,833) and claims priority to U.S. Provisional Patent Application Ser. No. 60/385,249 filed May 31, 2002 to Tokarski et at., entitled "Electrophotographic Photoreceptor With a Novel Charge Transport Compound," which are both incorporated herein by reference.

FIELD OF THE INVENTION

This invention relates to organophotoreceptors suitable for use in electro-photography and, more specifically, to organophotoreceptors having a charge transport compound comprising two hydrazone groups and a linking group comprising an aryl group.

BACKGROUND OF THE INVENTION

In electrophotography, an organophotoreceptor in the form of a plate, disk, sheet, belt, drum or the like having an electrically insulating photoconductive element on an electrically conductive substrate is imaged by first uniformly electrostatically charging the surface of the photoconductive layer, and then exposing the charged surface to a pattern of light. The light exposure selectively dissipates the charge in the illuminated areas, thereby forming a pattern of charged and uncharged areas. A liquid or solid toner is then deposited in either the charged or uncharged areas depending on the properties of the toner to create a toner image on the surface of the photoconductive layer. The resulting toner image can be transferred to a suitable receiving surface such as paper. The imaging process can be repeated many times to complete a single image and/or to reproduce additional images.

Both single layer and multilayer photoconductive elements have been used. In single layer embodiments, a charge transport material and charge generating material are combined with a polymeric binder and then deposited on the electrically conductive substrate. In multilayer embodiments, the charge transport material and charge generating material are in the form of separate layers, each of which can optionally be combined with a polymeric binder, deposited on the electrically conductive substrate. Two arrangements are possible. In one arrangement (the "dual layer" arrangement), the charge generating layer is deposited on the electrically conductive substrate and the charge transport layer is deposited on top of the charge generating layer. In an alternate arrangement (the "inverted dual layer" arrangement), the order of the charge transport layer and charge generating layer is reversed.

In both the single and multilayer photoconductive elements, the purpose of the charge generating material is to generate charge carriers (i.e., holes and/or electrons) upon exposure to light. The purpose of the charge transport compound is to accept at least one type of these charge carriers, generally holes, and transport them through the charge transport layer in order to facilitate discharge of a surface charge on the photoconductive element.

SUMMARY OF THE INVENTION

In a first aspect, the invention features an organophotoreceptor that includes:

(a) a charge transport compound having the formula

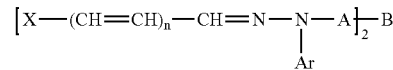

where n is an integer from 0 to 1;
X is an (N,N-disubstituted)arylamine group;
Ar is an aryl group or a heterocyclic group;
A is a first linking group with the formula —$(CH_2)_p$— which can be branched or linear, where p is an integer from 3 to 20 inclusive and where one or more methylene groups can be optionally replaced by O, S, a carbonyl group, urethane, urea, an ester group, a —$NR_{21}$ group, a $CHR_{22}$ group, or a $CR_{23}R_{24}$ group where $R_{21}$, $R_{22}$, $R_{23}$ and $R_{24}$ are, independently, H, hydroxyl, thiol, an amine group, an alkyl group, an alkaryl group, an aryl group, or part of a ring; and
B is a second linking group having the formula -Q-Z-Q'-, where Q and Q' are, independently, O, S, or $NR_1$; wherein when Q or Q' is $NR_1$ or Q=O and Q'=S, Z comprises an aryl group, and wherein when Q=Q'=S or Q=Q'=O, Z comprises a multi-ring conjugated group or -Y-W-Y'- wherein Y and Y' comprise, independently, an aryl group and W comprises a $CR_2R_3$ group; wherein $R_1$ is hydrogen or comprises an alkyl group or an aryl group; $R_2$ is a hydrogen or comprises an alkyl group, or an aryl group; and $R_3$ comprises an alkyl group or an aryl group or may form a ring structure along with the $R_2$ group;

(b) a charge generating compound; and
(c) an electrically conductive substrate over which the charge transport compound and the charge generating compound are located.

In a second aspect, the invention features an electrophotographic imaging apparatus that includes (a) a plurality of support rollers; and (b) the above-described organophotoreceptor operably coupled to the support rollers with motion of the support rollers resulting in motion of the organophotoreceptor. The apparatus can further comprise a liquid or solid toner dispenser.

In a third aspect, the invention features an electrophotographic imaging process that includes (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) contacting the surface with a toner to create a toned image; and (d) transferring the toned image to a substrate.

In a fourth aspect, the invention features charge transport compound having the formula

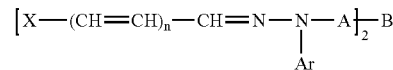

where n is an integer from 0 to 1;
X is an (N,N-disubstituted)arylamine group;
Ar is an aryl group or a heterocyclic group;
A is a first linking group with the formula —$(CH_2)_p$— which can be branched or linear, where p is an integer from 3 to 20 inclusive and where one or more methylene groups can be optionally replaced by O, S, a carbonyl group, urethane, urea, an ester group, a —$NR_{21}$ group, a $CHR_{22}$ group, or a $CR_{23}R_{24}$ group where $R_{21}$, $R_{22}$, $R_{23}$ and $R_{24}$ are, independently, H, hydroxyl, thiol, an amine group, an alkyl group, an alkaryl group, an aryl group, or part of a ring; and B is a second linking group having the formula -Q-Z-Q'-, where Q and Q' are, independently, O, S, or $NR_1$; wherein when Q or Q' is $NR_1$ or Q=O and Q'=S, Z comprises an aryl group, and wherein when Q=Q'=S or Q=Q'=O, Z comprises a multi-ring conjugated group or -Y-W-Y'- wherein Y and Y' comprise, independently, an aryl group and W comprises a $CR_2R_3$ group; wherein $R_1$ is hydrogen or comprises an alkyl group or an aryl group; $R_2$ is a hydrogen or comprises an alkyl group, or an aryl group; and $R_3$ comprises an alkyl group or an aryl group or may form a ring structure along with the $R_2$ group.

These charge transport compounds can further be used in the formation of organophotoreceptors as well as corresponding electrophotographic imaging apparatuses and electrophotographic imaging processes.

These photoreceptors can be used successfully with liquid toners to produce high quality images. The high quality of the images can be maintained after repeated cycling.

Other features and advantages of the invention will be apparent from the following description of the preferred embodiments thereof, and from the claims.

Herein, ranges involving integers include the end points of the range as possible values.

DETAILED DESCRIPTION OF PREFERRED EMBODIMENTS

Figure 1:
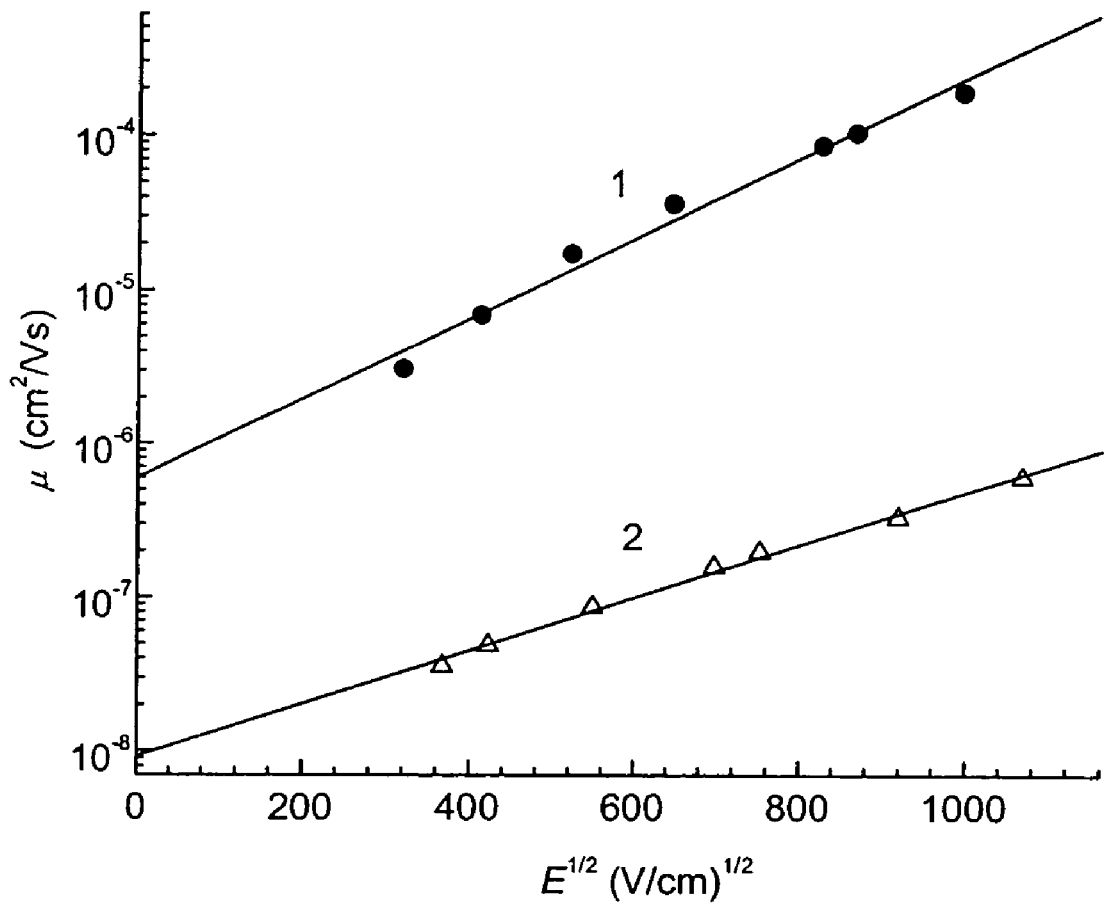
FIG. 1 is a graph depicting the dependence of hole mobility (μ) on electric field strength for two samples.

Charge transport compounds with desirable properties can be formed having two linked hydrazone groups with the linkage including aryl groups. These charge transport compounds have desirable properties as evidenced by their performance in organophotoreceptors for electrophotography. In particular, the charge transport compounds of this invention have high charge carrier mobilities and good compatibility with various binder materials; can be crosslinked in both the single and multilayer photoconductive elements; and possess excellent electrophotographic properties. The organophotoreceptor according to this invention has a high photosensitivity, a low residual potential, and high stabilities with respect to cycle testing, crystallization, and organophotoreceptor bending and stretching. The organophotoreceptors are particularly useful in laser printers and the like as well as photocopiers, scanners and other electronic devices based on electrophotography. The use of these charge transport compounds is described in more detail below in the context of laser printer use, although their application in other devices operating by electrophotography can be generalized from the discussion below.

To produce high quality images, particularly after multiple cycles, it is desirable for the charge transport compounds to form a homogeneous solution with the polymeric binder and remain approximately homogeneously distributed through the organophotoreceptor material during the cycling of the material. In addition, it is desirable to increase the amount of charge that the charge transport compound can accept (indicated by a parameter known as the acceptance voltage or "$V_{acc}$"), and to reduce retention of that charge upon discharge (indicated by a parameter known as the discharge voltage or "$V_{dis}$").

There are many charge transport compounds available for electrophotography. Examples of charge transport compounds are pyrazoline derivatives, fluorene derivatives, oxadiazole derivatives, stilbene derivatives, hydrazone derivatives, carbazole hydrazone derivatives, triaryl amines, polyvinyl carbazole, polyvinyl pyrene, polyacenaphthylene, or multi-hydrazone compounds comprising at least two hydrazone groups and at least two groups selected from the group consisting of triphenylamine and heterocycles such as carbazole, julolidine, phenothiazine, phenazine, phenoxazine, phenoxathiin, thianthrene, imidazole, benzothiazole, benzotriazole, benzoxazole, benzimidazole, quinoline, isoquinoline, quinoxaline, indole, indazole, pyrrole, purine, pyridine, pyridazine, pyrimidine, pyrazine, triazole, oxadiazole, tetrazole, thiadiazole, benzisoxazole, benzisothiazole, dibenzofuran, dibenzothiophene, thiophene, thianaphthene, quinazoline, or cinnoline. However, there is a need for other charge transport compounds to meet the various requirements of particular electrophotography applications.

In electrophotography applications, a charge generating compound within an organophotoreceptor absorbs light to form electron-hole pairs. These electron-hole pairs can be transported over an appropriate time frame under a large electric field to discharge locally a surface charge that is generating the field. The discharge of the field at a particular location results in a surface charge pattern that essentially matches the pattern drawn with the light. This charge pattern then can be used to guide toner deposition. The charge transport compounds described herein are especially effective at transporting charge, and in particular holes from the electron-hole pairs formed by the charge generating compound. In some embodiments, a specific electron transport compound can also be used along with the charge transport compound.

The layer or layers of materials containing the charge generating compound and the charge transport compounds are within an organophotoreceptor. To print a two dimensional image using the organophotoreceptor, the organophotoreceptor has a two dimensional surface for forming at least a portion of the image. The imaging process then continues by cycling the organophotoreceptor to complete the formation of the entire image and/or for the processing of subsequent images.

The organophotoreceptor may be provided in the form of a plate, a flexible belt, a disk, a rigid drum, a sheet around a rigid or compliant drum, or the like. The charge transport compound can be in the same layer as the charge generating compound and/or in a different layer from the charge generating compound. Additional layers can be used also, as described further below.

In some embodiments, the organophotoreceptor material comprises, for example: (a) a charge transport layer comprising the charge transport compound and a polymeric binder; (b) a charge generating layer comprising the charge generating compound and a polymeric binder; and (c) the electrically conductive substrate. The charge transport layer may be intermediate between the charge generating layer and the electrically conductive substrate. Alternatively, the charge generating layer may be intermediate between the charge transport layer and the electrically conductive substrate. In further embodiments, the organophotoreceptor material has a single layer with both a charge transport compound and a charge generating compound within a polymeric binder.

The organophotoreceptors can be incorporated into an electrophotographic imaging apparatus, such as laser printers. In these devices, an image is formed from physical embodiments and converted to a light image that is scanned onto the organophotoreceptor to form a surface latent image. The surface latent image can be used to attract toner onto the surface of the organophotoreceptor, in which the toner image is the same or the negative of the light image projected onto the organophotoreceptor. The toner can be a liquid toner or a dry toner. The toner is subsequently transferred, from the surface of the organophotoreceptor, to a receiving surface, such as a sheet of paper. After the transfer of the toner, the entire surface is discharged, and the material is ready to cycle again. The imaging apparatus can further comprise, for example, a plurality of support rollers for transporting a paper receiving medium and/or for movement of the photoreceptor, suitable optics to form the light image, a light source, such as a laser, a toner source and delivery system and an appropriate control system.

An electrophotographic imaging process generally can comprise (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) exposing the surface with a toner, such as a liquid toner that includes a dispersion of colorant particles in an organic liquid to create a toner image, to attract toner to the charged or discharged regions of the organophotoreceptor; and (d) transferring the toner image to a substrate.

This invention features an organophotoreceptor that includes a charge transport compound having the formula

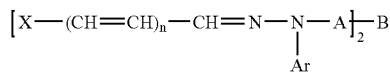

where n is an integer from 0 to 1;

X is an (N,N-disubstituted)arylamine group, such as a carbazole group, a julolidine group, or a p-(N,N-disubstituted)arylamine group (which can be a triarylamine, an alkyldiarylamine or a dialkylarylamine);

Ar is an aryl group or a heterocyclic group;

A is a first linking group with the formula —$(CH_2)_p$— which can be branched or linear, where p is an integer from 3 to 20 inclusive and where one or more methylene groups can be optionally replaced by O, S, a carbonyl group, urethane, urea, an ester group, a —$NR_{21}$ group, a $CHR_{22}$ group, or a $CR_{23}R_{24}$ group where $R_{21}$, $R_{22}$, $R_{23}$ and $R_{24}$ are, independently, H, hydroxyl, thiol, an amine group, an alkyl group, an alkaryl group, an aryl group, or part of a ring; and B is a second linking group having the formula -Q-Z-Q'-, where Q and Q' are, independently, O, S, or $NR_1$; wherein when Q or Q' is $NR_1$ or Q=O and Q'=S, Z comprises an aryl group, and wherein when Q=Q'=S or Q=Q'=O, Z comprises a multi-ring conjugated system or -Y-W-Y'- wherein Y and Y' comprise, independently, an aryl group and W comprises a $CR_2R_3$ group; wherein $R_1$ is hydrogen or comprises an alkyl group or an aryl group; $R_2$ is a hydrogen or comprises an alkyl group, or an aryl group; and $R_3$ comprises an alkyl group or an aryl group or may form a ring structure along with the $R_2$ group.

In describing chemicals by structural formulae and group definitions, certain terms are used in a nomenclature format that is chemically acceptable. The terms groups and moiety have particular meanings. The term group indicates that the generically recited chemical entity (e.g., alkyl group, phenyl group, julolidine group, (N,N-disubstituted) arylamine group, etc.) may have any substituent thereon which is consistent with the bond structure of that group. For example, alkyl group includes alkyl materials such as methyl ethyl, propyl iso-octyl, dodecyl and the like, and also includes such substituted alkyls such as chloromethyl, dibromoethyl, 1,3-dicyanopropyl, 1,3,5-trihydroxyhexyl, 1,3,5-trifluorocyclohexyl, 1-methoxy-dodecyl, phenylpropyl and the like. However, as is consistent with such nomenclature, no substitution would be included within the term that would alter the fundamental bond structure of the underlying group. For example, where a phenyl group is recited, substitution such as 1-hydroxyphenyl, 2,4-fluorophenyl, ortho-cyanophenyl, 1,3,5-trimethoxyphenyl and the like would be acceptable within the terminology, while substitution of 1,1,2,2,3,3-hexamethylphenyl would not be acceptable as that substitution would require the ring bond structure of the phenyl group to be altered to a non-aromatic form because of the substitution. Where the term moiety is used, such as alkyl moiety or phenyl moiety, that terminology indicates that the chemical material is not substituted.

Organophotoreceptors

The organophotoreceptor may be, for example, in the form of a plate, a flexible belt, a disk, a rigid drum, or a sheet around a rigid or compliant drum, with flexible belts and rigid drums generally being used in commercial embodiments. The organo-photoreceptor may comprise, for example, an electrically conductive substrate and a photoconductive element in the form of one or more layers. The organophotoreceptor comprises both a charge transport compound and a charge generating compound in a polymeric binder, which may or may not be in the same layer. For example, in some embodiments with a single layer construction, the charge transport compound and the charge generating compound are in a single layer. In other embodiments, however, the photoconductive element comprises a bilayer construction featuring a charge generating layer and a separate charge transport layer. The charge generating layer may be located intermediate between the electrically conductive substrate and the charge transport layer. Alternatively, the photoconductive element may have a structure in which the charge transport layer is intermediate between the electrically conductive substrate and the charge generating layer. In the dual layer embodiments, the charge generation layer generally has a thickness from about 0.5 to about 2 microns, and the charge transport layer has a thickness from about 5 to about 35 microns. In a single layer embodiment, the layer with the charge generating compound and the charge transport compound generally has a thickness from about 7 to about 30 microns.

The electrically conductive substrate may be flexible, for example in the form of a flexible web or a belt, or inflexible, for example in the form of a drum. A drum can have a hollow cylindrical structure that provides for attachment of the drum to a drive that rotates the drum during the imaging process. Typically, a flexible electrically conductive substrate comprises an electrically insulating substrate and a thin layer of electrically conductive material onto which the photoconductive material is applied.

The electrically insulating substrate may be paper or a film forming polymer such as polyethylene terephtalate, polyimide, polysulfone, polyethylene naphthalate, polypropylene, nylon, polyester, polycarbonate, polyvinyl fluoride, polystyrene and the like. Specific examples of polymers for supporting substrates included, for example, polyethersulfone (STABAR™ S-100, available from ICI), polyvinyl fluoride (TEDLAR®, available from E.I. DuPont de Nemours & Company), polybisphenol-A polycarbonate (MAKROFOL™, available from Mobay Chemical Company) and amorphous polyethylene terephthalate (MELINAR™, available from ICI Americas, Inc.). The electrically conductive materials may be graphite, dispersed carbon black, iodide, conductive polymers such as polypyroles and CALGON® conductive polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide. In embodiments of particular interest, the electrically conductive material is aluminum. Generally, the photoconductor substrate will have a thickness adequate to provide the required mechanical stability. For example, flexible web substrates generally have a thickness from about 0.01 to about 1 mm, while drum substrates generally have a thickness of from about 0.5 mm to about 2 mm.

The charge generating compound is a material which is capable of absorbing light to generate charge carriers, such as a dye or pigment. Examples of suitable charge generating compounds include metal-free phtbalocyanines (e.g., ELA 8034 metal-free phthalocyanine available from H.W. Sands, Inc.), metal phthalocyanines such as titanimn phthalocyanine, copper phthalocyanine, oxytitaniurn phthalocyanine, hydroxygallium phthalocyanine, squarylium dyes and pigments, hydroxy-substituted squarylium pigments, perylimides, polynuclear quinones available from Allied Chemical Corporation under the tradename INDOFAST® Double Scarlet, INDOFAST® Violet Lake B, INDOFAST® Brilliant Scarlet and INDOFAST® Orange, quinacridones available from DuPont under the tradename MONASTRAL™ Red, MONASTRAL™ Violet and MONASTRAL™ Red Y, naphthalene 1,4,5,8-tetracarboxylic acid derived pigments including the perinones, tetrabeazoporphyrins and tetranaphtbaloporphyrins, indigo- and thioindigo dyes, benzothioxanthene-derivatives, perylene 3,4,9,10-tetracarboxylic acid derived pigments, polyazo-pigments including bisazo-, trisazo- and tetrakisazo-pigments, polymethine dyes, dyes containing quinazoline groups, tertiary amines, amorphous selenium, selenium alloys such as selenium-tellurium, selenium-tellurim-arsenic and selenium-arsenic, cadmium sulfoselenide, cadmiumselenide, cadmium sulfide, and mixtures thereof. For some embodiments, the charge generating compound comprises oxytitanium phthalocyanine, hydroxygallium phthalocyanine or a combination thereof.

The photoconductive layer of this invention may contain an electron transport compound. Non-limiting examples of suitable electron transport compound include bromoanil, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitro-indeno4H-indeno[1,2-b]thiophene-4-one, and 1,3,7-trinitrodibenzo thiophene-5,5-dioxide, (2,3-diphenyl-1-indenylidene)malononitrile, 4H-thiopyran-1,1-dioxide and its derivatives such as 4-dicyanomethylene-2,6-diphenyl-4H-thiopyran-1,1-dioxide, 4-dicyanomethylene-2,6-di-m-tolyl-4H-thiopyran-1,1-dioxide, and unsym-metrically substituted 2,6-diaryl-4H-thiopyran-1,1-dioxide such as 4H-1,1-dioxo-2-(p-isopropylphenyl)-6-phenyl-4-(dicyanomethylidene)thiopyran and 4H-1,1-dioxo-2-(p-isopropylphenyl)-6-(2-thienyl)-4-(dicyanomethyl-idene) thiopyran, derivatives of phospha-2,5-cyclohexadiene, alkoxycarbonyl-9-fluorenylidene)malononitrile derivatives such as (4-n-butoxycarbonyl-9-fluorenylidene)malononitrile, (4-phenethoxycarbonyl-9-fluorenyl idene)malononitrile, (4-carbitoxy-9-fluorenylidene)malononitrile, and diethyl(4-n-butoxy carbonyl-2,7-dinitro-9-fluorenylidene)-malonate, anthraquinodimethane derivatives such as 11,11,12,12-tetracyano-2-alkylanthraquinodimethane and 11,11-dicyano-12,12-bis(ethoxycarbonyl)anthraquinodimethane, anthrone derivatives such as 1-chloro-10-[bis(ethoxycarbonyl)methylene]anthrone, 1,8-dichloro-10-[bis(ethoxycarbonyl) methylene]anthrone, 1,8-dihydroxy-10-[bis(ethoxycarbonyl)methylene]anthrone, and 1-cyano-10-[bis (ethoxycarbonyl)methylene)anthrone, 7-nitro-2-aza-9-fluroenylidene-malononitrile, diphenoquinone derivatives, benzoquinone derivatives, naphtoquinone derivatives, quinine derivatives, tetracyanoethylenecyanoethylene, 2,4,8-trinitro thioxantone, dinitrobenzene derivatives, dinitroanthracene derivatives, dinitroacridine derivatives, nitroanthraquinone derivatives, dinitroanthraquinone derivatives, succinic anhydride, maleic anhydride, dibromo maleic anhydride, pyrene derivatives, carbazole derivatives, hydrazone derivatives, N,N-dialkylaniline derivatives, diphenylamine derivatives, triphenylamine derivatives, triphenylmethane derivatives, tetracyano quinoedimethane, 2,4,5,7-tetranitro-9-fluorenone, 2,4,7-trinitro-9-dicyanomethylene fluorenone, 2,4,5,7-tetranitroxanthone derivatives, and 2,4,8-trinitrothioxanthone derivatives.

Suitable optional additives include, for example, light stabilizers, UV stabilizers, anti-oxidants, coupling agents, dispersing agents, curing agents, surfactants and combinations thereof.

Generally, a charge generation layer comprises a binder in an amount from about 10 to about 90 weight percent and in other embodiments in an amount from about 20 to about 75 weight percent, based on the weight of the charge generation layer. A charge transport layer generally comprises a binder in an amount from about 30 weight percent to about 70 weight percent. A single layer with a charge transport compound and a charge generating compound generally comprises a binder in an amount from about 10 weight percent to about 75 weight percent. The charge generation layer and/or the charge transport layer can further comprise an optional additive. A person of ordinary skill in the art will recognize that additional ranges of binder concentrations are contemplated and are within the present disclosure.

In some embodiments, the photoconductive layer is a single layer comprising a binder, a charge transport compound and a charge generation compound, and optionally an electron transport compound. The charge generation compound is in an amount from about 1 to about 25 weight percent and in other embodiments in an amount from about 2 to about 15 weight percent, based on the weight of the photoconductive layer. The charge transport compound is in an amount from about 25 to about 60 weight percent, based on the weight of the photoconductive layer, and in other embodiments in an amount from about 45 to about 55 weight percent, based on the weight of the photoconductive layer, with the remainder of the photoconductive layer comprising the binder, and optionally additives such as conventional additives. The optional electron transport compound in the photoconductive layer, when present, generally is in an amount from at least about 5 weight percent and, in other embodiments, from about 5 to about 25 weight percent and from about 10 to about 20 weight percent, based on the weight of the photoconductive layer. The photoconductive layer will typically have a thickness from about 7 to about 30 microns and may be formed in accordance with any appropriate technique known in the art, such as dip coating, spray coating, extrusion, and the like. A person of ordinary skill in the art will recognize that additional ranges of compositions and thickness within the explicit ranges are contemplated and are within the present disclosure.

For example, the photoconductive layer may be formed by dispersing or dissolving a charge generating compound, a charge transport compound, optionally an electron transport compound, and a polymeric binder in organic solvent, coating the dispersion and/or solution on the respective underlying layer and drying the coating. Preferably, the components are dispersed by high shear homogenization, ball-milling, attritor milling, high energy bead (sand) milling or other size reduction processes or mixing means known in the art for effecting particle size reduction in forming a dispersion.

The binder generally is capable of dispersing or dissolving the charge transport compound (in the case of the charge transport layer or a single layer construction) and/or the charge generating compound (in the case of the charge generating layer or a single layer construction). Examples of suitable binders for both the charge generating layer and charge transport layer generally include, for example, polystyrene-co-butadiene, polystyrene-co-acrylonitrile, modified acrylic polymers, polyvinyl acetate, styrene-alkyd resins, soya-alkyl resins, polyvinylchloride, polyvinylidene chloride, polyacrylonitrile, polycarbonates, polyacrylic acid, polyacrylates, polymethacrylates, styrene polymers, polyvinyl butyral, alkyd resins, polyamides, polyurethanes, polyesters, polysulfones, polyethers, polyketones, phenoxy resins, epoxy resins, silicone resins, polysiloxanes, poly (hydroxyether) resins, polyhydroxystyrene resins, novolak, poly(phenylglycidyl ether)-co-dicyclopentadiene, copolymers of monomers used in the above-mentioned polymers, and combinations thereof. In some embodiments, the binder is selected from the group consisting of polycarbonates, polyvinyl butyral, and a combination thereof. Examples of suitable polycarbonate binders include polycarbonate A which is derived from bisphenol-A, polycarbonate Z, which is derived from cyclohexylidene bisphenol, polycarbonate C, which is derived from methylbisphenol A, and polyestercarbonates. Examples of suitable of polyvinyl butyral are BX-1 and BX-5 form Sekisui Chemical Co. Ltd., Japan.

The photoreceptor may optionally have additional layers as well. Such additional layers can be, for example, a sub-layer and overcoat layers such as barrier layers, release layers, and adhesive layers. The release layer forms the uppermost layer of the photoconductor element. The barrier layer may be sandwiched between the release layer and the photoconductive element or used to overcoat the photoconductive element. The barrier layer provides protection from abrasion and carrier liquid to the underlayers. The adhesive layer locates and improves the adhesion between the photoconductive element, the barrier layer and the release layer, or any combination thereof. The sub-layer is a charge blocking layer and locates between the electrically conductive substrate and the photoconductive element. The sub-layer may also improve the adhesion between the electrically conductive substrate and the photoconductive element.

Suitable barrier layers include, for example, coatings such as crosslinkable siloxanol-colloidal silica coating and hydroxylated silsesquioxane-colloidal silica coating, and organic binders such as polyvinyl alcohol, methyl vinyl ether/maleic anhydride copolymer, casein, polyvinyl pyrrolidone, polyacrylic acid, gelatin, starch, polyurethanes, polyimides, polyesters, polyamides, polyvinyl acetate, polyvinyl chloride, polyvinylidene chloride, polycarbonates, polyvinyl butyral, polyvinyl acetoacetal, polyvinyl formal, polyacrylonitrile, polymethyl methacrylate, polyacrylates, polyvinyl carbazoles, copolymers of monomers used in the above-mentioned polymers, vinyl chloride/vinyl acetate/vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above barrier layer polymers optionally may contain small inorganic particles such as fumed silica, silica, titania, alumina, zirconia, or a combination thereof. Barrier layers are described further in U.S. Pat. No. 6,001,522 to Woo et al., entitled "Barrier Layer For Photoconductor Elements Comprising An Organic Polymer And Silica," incorporated herein by reference. The release layer topcoat may comprise any release layer composition known in the art. In some embodiments, the release layer is a fluorinated polymer, siloxane polymer, fluorosilicone polymer, silane, polyethylene, polypropylene, polyacrylate, or a combination thereof. The release layers can comprise crosslinked polymers.

The release layer may comprise, for example, any release layer composition known in the art. In some embodiments, the release layer comprises a fluorinated polymer, siloxane polymer, fluorosilicone polymer, silane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In further embodiments, the release layers comprise crosslinked polymers.

The overcoat layer may comprise an electron transport compound as described further in copending U.S. patent application Ser. No. 10/396,536, filed on Mar. 25, 2003 to Zhu et al. entitled, "Organoreceptor With An Electron Transport Layer," now U.S. Pat. No. 6,890,693, issued May 10, 2005, incorporated herein by reference. For example, an electron transport compound as described above may be used in the release layer of this invention. The electron transport compound in the overcoat layer can be in an amount of from about 10 to about 50 weight percent, and in other embodiments in an amount of from about 20 to about 40 weight percent, based on the weight of the release layer. A person of ordinary skill in the art will recognize that additional ranges of composition within the explicit ranges are contemplated and are within the present disclosure.

Generally, adhesive layers comprise a film forming polymer, such as polyester, polyvinylbutyral, polyvinylpyrolidone, polyurethane, polymethyl methacrylate, poly(hydroxy amino ether) and the like.

Sub-layers can comprise, for example, polyvinylbutyral, organosilanes, hydrolyzable silanes, epoxy resins, polyesters, polyamides, polyurethanes, silicones and the like. In some embodiments, the sub-layer has a dry thickness between about 20 Angstroms and about 2,000 Angstroms. Sublayers containing metal oxide conductive particles can be between about 1 and about 25 microns thick. A person of ordinary skill in the art will recognize that additional ranges of compositions and thicknesses within the explicit ranges are contemplated and are within the present disclosure.

The charge transport compounds as described herein, and photoreceptors including these compounds, are suitable for use in an imaging process with either dry or liquid toner development. Liquid toner development can be desirable because it offers the advantages of providing higher resolution images and requiring lower energy for image fixing compared to dry toners. Examples of suitable liquid toners are known in the art. Liquid toners generally comprise toner particles dispersed in a carrier liquid. The toner particles can comprise a colorant/pigment, a resin binder, and/or a charge director. In some embodiments of liquid toner, a resin to pigment ratio can be from 2:1 to 10:1, and in other embodiments, from 4:1 to 8:1. Liquid toners are described further in Published U.S. Patent Applications 2002/0128349, entitled "Liquid Inks Comprising A Stable Organosol," 2002/0086916, entitled "Liquid Inks Comprising Treated Colorant Particles," and 2002/0197552, entitled "Phase Change Developer For Liquid Electrophotography," all three of which are incorporated herein by reference.

Charge Transport Compound

In some embodiments, the organophotoreceptors as described herein can comprise a two hydrazone based compound as a charge transport compound having the formula

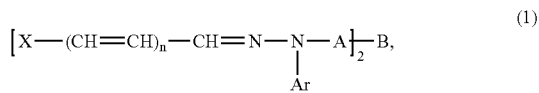

(1)

where n is an integer from 0 to 1; X is an (N,N-disubstituted) arylamine group, such as a carbazole group, a julolidine group, or a p-(N,N-disubstituted)arylamine group (which can be a triarylamine, an alkldiarylamine or a dialkylarylamine); Ar is an aryl group or a heterocyclic group; A is a first linking group; and B is a second linking group. The first linking group A has the formula $—CH_2)_p—$ which can be branched or linear, where p is an integer from 3 to 20 inclusive and where one or more methylene groups can be optionally replaced by O, S, a carbonyl group, urethane, urea, an ester group, a $—NR_{21}$ group, a $CHR_{22}$ group, or a $CR_{23}R_{24}$ group where $R_{21}$, $R_{22}$, $R_{23}$ and $R_{24}$ are, independently, H, hydroxyl, thiol, an amine group, an alkyl group, an alkaryl group, an aryl group, or part of a ring. The second linking group B has the formula -Q-Z-Q'-, where Q and Q' are, independently, O, S, or $NR_1$; wherein when Q or Q' is $NR_1$ or Q=O and Q'=S, Z comprises an aryl group, and wherein when Q=Q'=S or Q=Q'=O, Z comprises a multi-ring conjugated system or -Y-W-Y'- wherein Y and Y' comprise, independently, an aryl group and W comprises a $CR_2R_3$ group; wherein $R_1$ is hydrogen or comprises an alkyl group or an aryl group; $R_2$ is a hydrogen or comprises an alkyl group, or an aryl group; and $R_3$ comprises an alkyl group or an aryl group or may form a ring structure along with the $R_2$ group.

Non-limiting examples of the charge transport compound of this invention have the following formula

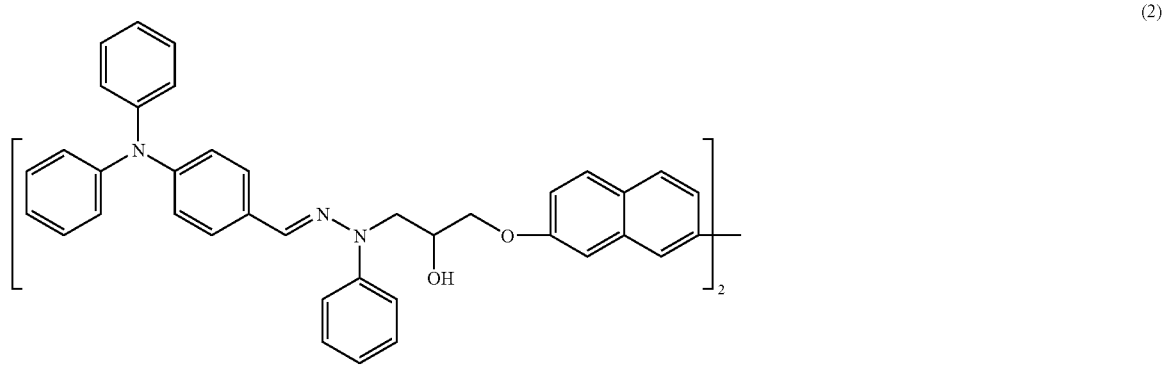

(2)

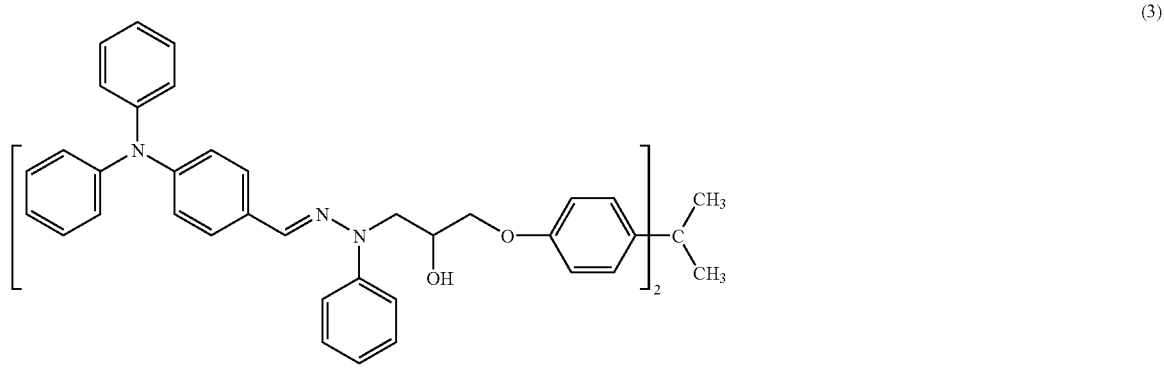

(3)

-continued

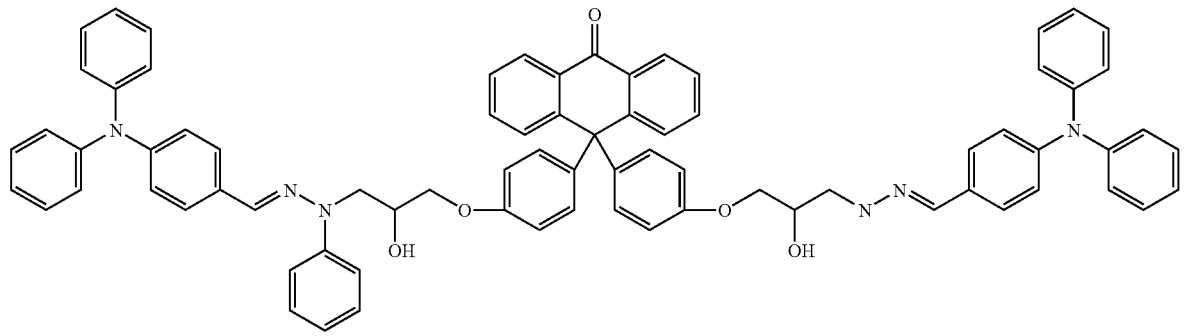

(4)

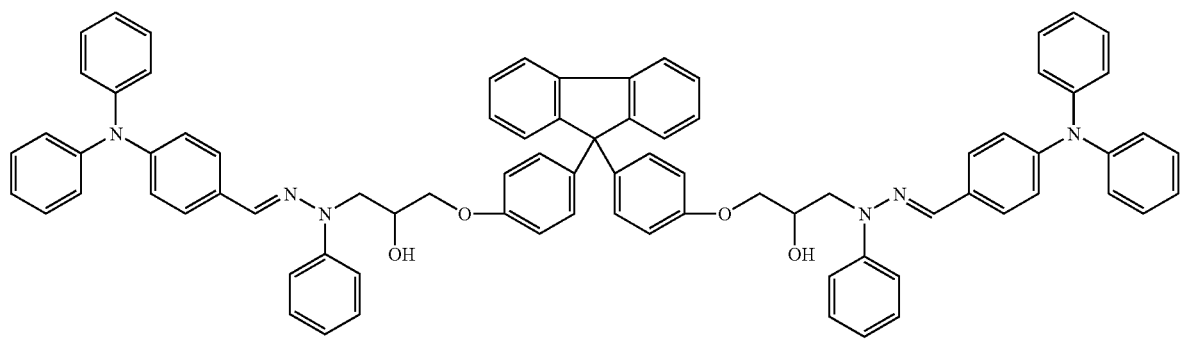

(5)

Synthesis of Charge Transport Compounds

The charge transport compounds with two linked hydrazones are based on the reaction of an arylhydrazone compound with a first linker generally comprising a halogen functional group and a second functional group reactive with a functional group with active hydrogens and a second linker comprising two functional groups, with each generally having active hydrogens. The second linker connects the two hydrazones by way of the first linker. The arylhydrazone bonded to the first linker can be referred to as a derivatized hydrazone. The derivatized hydrazone can be formed by forming an aryl hydrazone from the reaction of an aryl aldehyde or aryl ketone with a hydrazine. The aryl hydrazone can react with the halogen functional group of the first linker to add the linker onto the aryl hydrazone at the single bonded nitrogen of the hydrazone. The first linker has a functional group suitable for reaction with a functional group with active hydrogens such that the derivatized aryl hydrazone is formed when the aryl hydrazone bonds with the first linker.

In summary, an aryl hydrazone is formed by reacting an aryl aldehyde or aryl ketone with a hydrazine. The aryl hydrazone is reacted with a first linker to form a derivatized aryl hydrazone. The derivatized aryl hydrazone is reacted with the second linker to form the charge transport compound.

With respect to appropriate aryl hydrazines, phenylhydrazine and benzylhydrazine hydrochloride are commercially available from Aldrich (Milwaukee, Wis.). Heterocyclic aryl groups can be provided through the use of other hydrazines, such as 2-hydrazinophyridine (Aldrich) or 2-hydrazinopyrinidine (Interchim, France). Other aryl hydrazines can be formed based on derivatives the commerically available compounds or by other hydrazine derivatized aromatic compounds synthesized by appropriate approaches including those known in the art.

With respect to representative aryl aldehydes, 4-(diphenylamino) benzaldehyde and 9-ethyl-3-carbazolcarboxyaldehyde are utilized in the Examples below. Both of theses aryl aldehydes are available commercially from Aldrich, Milwaukee, Wis. In addition, julolidine aldehyde can be synthesized from julolidine, which also is available commercially from Aldrich, Milwaukee, Wis. Specifically, julolidine (100 g, 0.6 moles) can be dissolved in 200 ml warm N, N-dimethylformamide (DMF, commercially obtained from Aldrich) in a 500 ml three neck round bottom flask. After the julolidene is dissolved, the flask is cooled to 0° C. in an ice bath. Then, $POCl_3$ (107 g, 0.7 mole; commercially available from Aldrich) can be added dropwise via a dropping funnel while keeping the temperature below 5° C. After the addition of $POCl_3$ is completed, the flask is warmed to room temperature and placed in a steam bath where it is stirred for a period of 1 hour. The flask is cooled to room temperature and the solution is added slowly, with good agitation, to a large excess of distilled water. Stirring is continued for an additional 2 hours. The solid julolidine aldehyde is filtered off and washed repeatedly with water until the effluent water becomes neutral. The product can be dried at 50° C. in a vacuum oven for 4 hours.

For embodiments of the charge transport compound formula described above in which n=1 and X=p-dimethylaminophenyl group, p-dimethylaminocinnamaldehyde (commercially available from Aldrich) is used in place of p-dimethylaminophenylaldehyde. For n=1 and X=a carbazole group, 9-ethyl-3-carbazolecinnamaldehyde is used instead of 9-ethyl-3-carbazolecaboxaldehyde. For n=1 and X=triphenylamine, 4-(diphenylamino)cinnamaldehyde is used instead of 4-(diphenylamino)benzaldehyde. For n=1 and X=julolidine, julolidinecinnamaldehyde is used instead of julolidinealdehyde. Other aryl aldehydes for the formation of charge transport compounds with n=1 can be similarly selected. All other reactions are similar and described in the experimental section. The synthesis of 9-ethyl-3-carbazolecinnamaldehyde, 4-(diphenylamino)cinnamaldehyde and julolidine-cinnamaldehyde can be carried out by analogy with the commercial synthesis approach for p-dimethylaminocinnamaldehyde.

Having obtained a selected hydrazine and aryl aldehyde/ketone, the hydrazones can be synthesized from the reaction of the selected hydrazine with the aryl aldehyde/ketone in an alkaline catalyzed reaction. In some embodiments, the hydrazines are obtained in an acidified hydrochloride form. For these embodiments, the hydrazine hydrochloride can be reacted with an aqueous carbonate base and stirring of the mixture. An excess of carbonate base can be added, such as 1.2 moles of potassium carbonate for embodiments with one mole of hydrazine hydrochloride per mole hydrazine or 2.4 moles of potassium carbonate for embodiments with one mole of hydrazine dihydrochloride per mole hydrazine.

With respect to the first linker, noted as A following binding, the linker compound can comprise a halide group, such as Cl, for binding with the single bonded nitrogen of the hydrazone, and a second functional group for bonding with a thiol group of the second linker, noted as B following bonding. The second functional group of the first linker can be for example, an epoxy/oxirane group that reacts with a functional group with active hydrogens to form a secondary alcohol, a halide group reacts with an active hydrogen to form an ether, an amine or thioether, or a carbonyl halide or acid anhydride group to form an ester, an amide or a thiol carbonyl (R—SCO—R') group, as appropriate for the active hydrogen group. Additional suitable reactions involving active hydrogen groups can be used with appropriate functional groups on the first linker.

In the examples below, the second linker is an aromatic diol. Specifically, the second linker was 2,2'-bi-7-naththol (commercially available from Aldrich), 4,4'-isopropylidene-diphenol (Bisphenol A, commercially available from Aldrich, Milwaukee, Wis.), 10,10-bis(4-hydroxyphenyl)anthrone (commercially available from Chimreativ, Russia), or 4,4'-(9-fluorenylidene)diphenol (commercially available from Aldrich). Other representative second linkers are also commercially available from Aldrich including, for example, phenylene diamine, aminophenol, hydroxythiophenol, aminothiophenol and 4,4'-thiolbisbenzenethiol. Other suitable second linkers are available commercially from Aldrich and other suppliers and can be synthesized using available techniques by a person or ordinary skill in the art.

The particular reaction conditions for bonding the first linker with the hydrazone and with the second linker can be selected by a person of ordinary skill in the art based on the particular reaction involved and the discussion herein. Appropriate conditions for the reaction of epichlorohydrin with various hydrazones and a is described in detail in the Examples. In particular, the synthesis and characterization of compounds 2–5 are described in detail in the Examples.

Organophotoreceptor (OPR) Preparation Methods

Following conventional terminology, the number of layers in the OPR refers to the layers with charge transport compounds and/or charge generating compounds. Thus, the presence of overlayers, underlayers, release layers and the like do not alter the single layer versus dual layer terminology.

Positive Inverted Dual Layer OPR

A positive polarity, inverted dual layer organic photoreceptor can be prepared by incorporating a charge transfer compound disclosed herein into the charge transport layer and then over coating this layer with a charge generation solution to form a charge generation layer. The positive inverted dual layer is designed to operate with a positive surface charge that is discharge upon illumination at the point of illumination. An example of a specific approach for forming this structure is presented below.

In one embodiment a charge transport solution comprising a 1:1 ratio by weight of a charge transfer compound as described herein to a binder, such as polycarbonate Z binder (commercially available from Mitsubishi Gas Chemical under the trade name LUPILON™ Z-200 resin), can be prepared by combining a solution of 1.25 g of one of the charge transfer compounds as described herein in 8.0 g of tetrahydrofuran with 1.25 g of polycarbonate Z in 6.25 g of tetrahydrofuran. The charge transport solution can be hand-coated onto a 76-micrometer (3-mil) thick aluminized poLyester substrate (such as a MELINEX® 442 polyester film from Dupont having a 1 ohm/square aluminum vapor coat) having a 0.3-micron polyester resin sub-layer (VITEL® PE-2200 from Bostik Findley, Middletown, Mass.). A knife coater, set to a 51-micrometer (2-mil) orifice between the blade and polyester, can be used to prepare a film with an 8–10-micron thickness after drying the wet film in an oven at 110° C. for 5–10 min.

A dispersion for forming a charge generation layer can be prepared by micronising 76.1 g of oxytitanium phthalocyanine pigment (H.W. Sands Corp., Jupiter, Fla.), 32.6 g of S-LEC B BX-5 polyvinylbutryal resin (Sekisui Chemical Co. Ltd.), and 641.3 g of methyl ethyl ketone, using a horizontal sand mill operating in recycle mode for 8 hours. After milling, the charge generation layer base can be diluted with methyl ethyl ketone to decrease the total solids of the solution to 4.0 wt %. The charge generation solution can be hand-coated onto the charge transport layer using a knife coater, set to a 20–25 micron (0.8–1.0 mil) orifice between the blade and charge transfer layer to prepare a sub-micron thick charge generation layer (CGL) film after drying the wet film in an oven at 110° C. for 3–5 min.

Negative Dual Layer OPR

A negative polarity, dual layer organic photoreceptor can be prepared forming a charge generation layer and then incorporating a charge transfer compound disclosed herein into a solution and coating this solution over the charge generation layer to form a charge transfer layer. A negative dual layer is designed to operate with a negative surface charge that is discharged upon illumination at the point of illumination. A specific example for forming a negative dual layer is described below.

In one embodiment, a charge generation layer mill-base dispersion can be prepared by micronising 76.1 g of oxytitanium phthalocyanine pigment, 32.6 g of S-LEC B BX-5 polyvinylbutryal resin (Sekisui Chemical Co. Ltd.), and 641.3 g of methyl ethyl ketone, using a horizontal sand mill operating in recycle mode for 8 hours. Following milling the charge generating layer base can be diluted with methyl ethyl ketone to decrease the total solids of the solution to 4.0 wt %. The charge generation solution can be hand-coated onto a 76-micrometer (3-mil) thick aluminized polyester substrate (MELINEX® 442 polyester film from Dupont having a 1 ohm/square aluminum vapor coat) having a 0.3-micron polyester resin sub-layer (VITEL® PE-2200 from Bostik Findley, Middletown, Mass.). A knife coater, set to a 20–25 micron (0.8–1.0 mil) orifice between the blade and substrate, can be used to prepare the sub-micron thick charge generating layer film after drying the wet film in an oven at 110° C. for 3–5 min.

A charge transport solution comprising a 1:1 ratio by weight of a charge transfer compound described herein to polycarbonate Z binder is prepared by combining a solution of 1.25 g of the charge transfer compound in 8.0 g of tetrahydrofuran with 1.25 g of polycarbonate Z in 6.25 g of tetrahydrofuran. A knife coater, set to a 51-micrometer (2-mil) orifice between the blade and polyester, can be used to prepare an 8–10-micron thick film after drying the wet film in an oven at 110° C. for 5–10 min.

Single Layer OPR

A single layer organic photoreceptor can be prepared by incorporating a charge transfer compound disclosed herein along with a charge generating composition into a single coating solution and then coating this solution over a suitable substrate. A single layer OPR are designed to operate with a surface charge, which may be positive or negative, that is discharged upon illumination at the point of illumination in which the charge is generated in a layer and transported through that layer.

In practice, single layer OPRs are used predominantly with positive surface charges. In general, through the photoconductive and semiconductive materials of interest, electrons have a significantly lower mobility than holes. With low concentrations of charge generating pigment compounds to limit charge trapping in a single layer structure, the electron-hole pairs can be generated some distance from the surface of the OPR after light is absorbed. However, the electron-hole pairs still tend to be closer to the surface than the substrate, such that the electron has less distance to travel than the hole in a positive single layer OPR. The hole from the electron-hole pair can transport through the remaining portion of the OPR to the underlying substrate. Thus, while electrons may travel some distance to neutralize positive charges at the surface of a positively charged OPR, the electrons would still have significantly larger distance to travel to the substrate in a negative single layer OPR. For single layer embodiments, it can be desirable to include an optional electron transport compound to facilitate the electron transport.

However, the use of a dual layer positive OPR is complicated by the formation of a thin charge generating layer over a charge transport layer due to processing complications of dip coating and solvent selection. Also, the thin charge generating layer can be abraded away in use without a good overcoat layer. Thus, a single layer positive OPR may offer some advantages over a positive dual layer system. Since the formation of negative dual layer OPRs do not have the complications of positive dual layer OPRs and since limited electron mobility hinders operation of negative single layer OPRs, negative single layer OPRs generally are less desirable although they are within the scope of the present disclosure for incorporation of the improved charge transport compounds described herein.

In one embodiment especially for the preparation of a single layer OPR, a charge transport pre-mix solution containing a 1:1 ratio by weight of a charge transport compound disclosed herein to polycarbonate Z binder can be prepared by combining a solution of 1.25 g of the charge transfer compound in 8.0 g of tetrahydrofuran with 1.25 g of polycarbonate Z in 6.25 g of tetrahydrofuran. A charge generating layer mill-base dispersion can be prepared by micronising 76.1 g of oxytitanium phthalocyanine pigment, 32.6 g of polycarbonate Z binder resin, and 641.3 g of tetrahydrofuran, using a horizontal sand mill operating in pass mode for 6–8 passes. An electron transport pre-mix solution containing a 1:1.4 ratio of (4-n-butoxycarbonyl-9-fluorenylidene) malononitrile electron transport compound to Polycarbonate Z binder can be prepared by combining a solution of 1.25 g of one of the electron transporting material in 8.0 g of tetrahydrofuran with 1.75 g of polycarbonate Z in 9 g of tetrahydrofuran.

The single layer coating solution can be prepared by combining 14 g of the charge transport pre-mix, 4.08 g of the electron transport premix and 1.92 g of the charge generating layer mill-base dispersion. The single layer solution can be hand-coated onto a 76-micrometer (3-mil) thick aluminized polyester substrate (MELINEX® 442 polyester film from Dupont having a 1 ohm/square aluminum vapor coat) having a 0.3-micron polyester resin sub-layer (VITEL® PE-2200 from Bostik Findley, Middletown, Mass.). A knife coater, set to a 50–75 micron (2–3 mil) orifice between the blade and substrate, can be used to prepare a single layer film with an 8–10 micron thickness after drying the wet film in an oven at 110° C. for 5–10 min.

The invention will now be described further by way of the following examples.

EXAMPLES

Example 1

Synthesis of an Electron Transport Compound

This example describes the preparation of (4-n-butoxycarbonyl-9-fluorenylidene) malononitrile, for convenience to be designated ETM-2.

A 460 g quantity of concentrated sulfuric acid (4.7 moles, analytical grade, commercially obtained from Sigma-Aldrich, Milwaukee, Wis.) and 100 g of diphenic acid (0.41 mole, commercially obtained from Acros Fisher Scientific Company Inc., Hanover Park, Ill.) were added to a 1-liter 3-neck round bottom flask, equipped with a thermometer, mechanical stirrer and a reflux condenser. Using a heating mantle, the flask was heated to 135–145° C. for 12 minutes, and then cooled to room temperature. After cooling to room temperature, the solution was added to a 4-liter Erlenmeyer flask containing 3 liter of water. The mixture was stirred mechanically and was boiled gently for one hour. A yellow solid was filtered out hot, washed with hot water until the pH of the wash-water was neutral, and was air-dried overnight. The yellow solid was fluorenone-4-carboxylic acid. The yield was 75 g (80%). The product was then characterized. The melting point (m.p.) was found to be 223–224° C. A $^1$H-NMR spectrum of fluorenone-4-carboxylic acid was obtained in $d_6$-DMSO solvent with a 300 MHz NMR from Bruker Instrument. The peaks were found at (ppm) $\delta$=7.39–7.50 (m, 2H); $\delta$=7.79–7.70 (q, 2H); $\delta$=7.74–7.85 (d, 1H); $\delta$=7.88–8.00 (d, 1H); and $\delta$=8.18–8.30 (d, 1H), where d is doublet, t is triplet, m is multiplet; dd is double doublet, q is quintet.

A 70 g (0.312 mole) quantity of fluorenone-4-carboxylic acid, 480 g (6.5 mole) of n-butanol (commercially obtained from Fisher Scientific Company Inc., Hanover Park, Ill.), 1000 ml of toluene and 4 ml of concentrated sulfuric acid were added to a 2-liter round bottom flask equipped with a mechanical stirrer and a reflux condenser with a Dean Stark apparatus. With aggressive agitation and refluxing, the solution was refluxed for 5 hours, during which ~6 g of water were collected in the Dean Stark apparatus. The flask was cooled to room temperature. The solvents were evaporated and the residue was added, with agitation, to 4-liter of a 3% sodium bicarbonate aqueous solution. The solid was filtered off, washed with water until the pH of the wash-water was neutral, and dried in the hood overnight. The product was n-butyl fluorenone-4-carboxylate ester. The yield was 70 g (80%). A $^1$H-NMR spectrum of n-butyl fluorenone-4-carboxylate ester was obtained in CDCl$_3$ with a 300 MHz NMR from Bruker Instrument. The peaks were found at (ppm) δ=0.87–1.09 (t, 3H); δ=1.42–1.70 (m, 2H); δ=1.75–1.88 (q, 2H); δ=4.26–4.64 (t, 2H); δ=7.29–7.45 (m, 2H); δ=7.46–7.58 (m, 1H); δ=7.60–7.68 (dd, 1H); δ=7.75–7.82 (dd, 1H); δ=7.90–8.00 (dd, 1H); δ=8.25–8.35 (dd, 1H).

A 70 g (0.25 mole) quantity of n-butyl fluorenone-4-carboxylate ester, 750 ml of absolute methanol, 37 g (0.55 mole) of malononitrile (commercially obtained from Sigma-Aldrich, Milwaukee, Wis.), 20 drops of piperidine (commercially obtained from Sigma-Aldrich, Milwaukee, Wis.) were added to a 2-liter, 3-neck round bottom flask equipped with a mechanical stirrer and a reflux condenser. The solution was refluxed for 8 hours and the flask was cooled to room temperature. The orange crude product was filtered, washed twice with 70 ml of methanol and once with 150 ml of water, and dried overnight in the hood. This orange crude product was recrystalized from a mixture of 600 ml of acetone and 300 ml of methanol using activated charcoal. The flask was placed at 0° C. for 16 hours. The crystals were filtered and dried in a vacuum oven at 50° C. for 6 hours to obtain 60 g of pure (4-n-butoxycarbonyl-9-fluorenylidene) malononitrile. The melting point (m.p.) of the solid was found to be 99–100° C. A $^1$H-NMR spectrum of (4-n-butoxycarbonyl-9-fluorenylidene) malononitrile was obtained in CDCl$_3$ with a 300 MHz NMR from Bruker Instrument. The peaks were found at (ppm) δ=0.74–1.16 (t, 3H); δ=1.38–1.72 (m, 2H); δ=1.70–1.90 (q, 2H); δ=4.29–4.55 (t, 2H); δ=7.31–7.43 (m, 2H); δ=7.45–7.58 (m, 1H); δ=7.81–7.91 (dd, 1H); δ=8.15–8.25 (dd, 1H); δ=8.42–8.52 (dd, 1H ); δ=8.56–8.66 (dd, 1H).

Example 2

Synthesis of Epoxy-Derivitized Hydrazones

This example presents the synthesis of two epoxy-derivitized hydrazones. These hydrazones can be reacted with a linker compound to form charge transfer compounds as described herein.

Preparation of 9-Ethyl-3-carbazolecarbaldehyde N-2,3-epoxypropyl-N-phenylhydrazone A mixture of 9-ethyl-3-carbazolecarbaldehyde phenylhydrazone (3.1 g, 0.01 mol), 85% powdered potassium hydroxide (2.0 g, 0.03 mol) and anhydrous potassium carbonate (~5 g) in 25 ml of epichlorohydrin was stirred vigorously at 55–60° C. for 1.5–2 h. The course of the reaction was monitored using thin layer chromatography on silica gel 60 F254 plates (commercially obtained from Merck) using a 1:4 volume per volume mixture of acetone and hexane as the eluant. After termination of the reaction, the mixture was cooled to room temperature, diluted with ether and washed with water until the wash water was neutral in pH. The organic layer was dried over anhydrous magnesium sulfate, treated with activated charcoal, and filtered. Ether was removed, and the residue was dissolved in the mixture of toluene and 2-propanol in 1:1 ratio by volume. The crystals formed upon standing were filtered off, and washed with 2-propanol to give 3.0 g (81.2%) of 9-ethyl-3-carbazolecarbaldehyde N-2,3-epoxypropyl-N-phenylhydrazone. The solid product had a melting point (m.p.) of 136–137° C. after being recrystallized from a mixture of toluene and 2-propanol in 1:1 ratio by volume. A $^1$H-NMR spectrum of 9-ethyl-3-carbazolecarbaldehyde N-2,3-epoxypropyl-N-phenylhydrazone was obtained in CDCl$_3$ with a 250 MHz NMR. The peaks were found at (ppm) δ=8.35 (s, 1H, 4-H$_{Ht}$); δ=8.14 (d, J=7,8 Hz, 1H, 1-H$_{Ht}$); δ=7.93 (d, J=7,6 Hz, 1H, 2-H$_{Ht}$); δ=7.90 (s, 1H, CH=N); δ=7.54–7.20 (m, 8H, Ph, Ht); δ=6.96 (t, J=7.2 Hz, 1H, 4-H$_{Ph}$); δ=4.37 (m, 3H, CH$_2$CH$_3$, one of the NCH$_2$ protons); δ=4.04 (dd, J$_1$=4.3 Hz, J$_2$=16.4 Hz, 1H, next of the NCH$_2$ protons); δ=3.32 (m, 1H, CH); δ=2.88 (dd, 1H, part of the ABX system, cis-H$_A$ of CH$_2$O, J$_{AX}$=2.6 Hz, J$_{AB}$=4.9 Hz); δ=2.69 (dd, 1H, part of the ABX system, trans-H$_B$ of CH$_2$O, J$_{BX}$=4.0 Hz); δ=1.44 (t, J=7.2 Hz, 3H, CH$_3$). An elemental analysis found the following weight percents of the elements: C, 78.32; H, 6.41; N, 11.55. which compares with the following calculated elemental weight percent for a compound with the formula C$_{24}$H$_{23}$N$_3$O: C, 78.02; H, 6.28; N, 11.37.

Preparation of 4-(Diphenylamino)benzaldehyde N-2,3-epoxypropyl-N-phenylhydrazone 4-(Diphenylamino)benzaldehyde N-2,3-epoxypropyl-N-phenylhydrazone was prepared according to the preparation procedure above for 9-ethyl-3-carbazolecarbaldehyde N-2,3-epoxypropyl-N-phenylhydrazone except that 9-ethyl-3-carbazolecarbaldehyde phenylhydrazone was replaced by 4-(diphenylamino) benzaldehyde phenylhydrazone (3.5 g, 0.01 mol). The yield of 4-(diphenylamino) benzaldehyde N-2,3-epoxypropyl-N-phenylhydrazone was 3.0 g (71.4%). The melting point (m.p.) of the product was 141–142.5° C. after being recrystallized from toluene. A $^1$H-NMR spectrum of 4-(diphenylamino) benzaldehyde N-2,3-epoxypropyl-N-phenylhydrazone was obtained in CDCl$_3$ with a 250 MHz NMR. The peaks were found at (ppm) δ=7.65–6.98 (m, 19H, CH=N, Ar); δ=6.93 (t, J=7.2 Hz, 1H, 4-H$_{Ph}$); δ=4.35 (dd, 1H, part of the ABX system, cis-H$_A$ of NCH$_2$, J$_{AX}$=2.4 Hz, J$_{AB}$=16.4); δ=3.99 (dd, 1H, part of the ABX system, trans-H$_B$ of NCH$_2$, J$_{BX}$=4.1 Hz); δ=3.26 (m, 1H, CH); δ=2.84 (dd, 1H, part of the ABX system, cis-H$_A$ of CH$_2$O, J$_{AX}$=2.7 Hz, J$_{AB}$=4.8 Hz); δ=2.62 (dd, 1H, part of the ABX system, trans-H$_B$ of CH$_2$O, J$_{BX}$=4.1 Hz). An elemental analysis found the following weight percents of the elements: C, 80.02; H, 6.31; N, 9.91. which compares with the following calculated elemental weight percent for a compound with the formula C$_{28}$H$_{25}$N$_3$O: C, 80.16; H, 6.01; N, 10.02.

Example 3

Synthesis of Charge Transport Compounds

This examples describes the synthesis of four charge transport compounds corresponding to compounds 2–5 above.

Preparation of Compound 2

A mixture of 8.8 g (21.0 mmol) of 4-(diphenylamino) benzaldehyde N-2,3-epoxypropyl-N-phenylhydrazone, which was synthesized as described above in Example 2, and 2.86 g (10.0 mmol) of 2,2'-bi-7-naphtol (commercially obtained from Aldrich, Milwaukee, Wis.) were dissolved in 20 ml of 2-butanone and 1.2 ml (8.90 mmol) of triethylamine (TEA, commercially obtained from Aldrich, Milwaukee, Wis.) were added. The mixture was refluxed for 15 hours until the 2,2'-bi-7-naphtol and its monosubstituted derivative disappeared. The course of the reaction was monitored by thin layer chromatography on silica gel 60 F254 plates (commercially obtained from Merck) using a 3:1 volume per volume mixture of ether and hexane as the eluant. At the end of the reaction, the solvent was evaporated and the residue was purified by chromatography using a column packed with silica gel (grade 62, 60–200 mesh, commercially obtained from Aldrich, Milwaukee, Wis.) and a 4:1 volume per volume solution of hexane and propanone as the eluant to yield a solid. A 20 weight % solution of this material in toluene was prepared and then poured with intensive stirring into a 10-fold excess of hexane to yield 7.5 g (67.0%) of compound 2 as a yellowish powder. The infrared absorption spectrum resulted in the identification of the following peaks; IR(KBr) (frequency in cm$^{-1}$): 3620–3180 (OH); 3060, 3040 (CH$_{aromatic}$); 2945, 2920, 2895 (CH$_{aliphatic}$); 805, 760, 690 (CH=CH of naphtalene, mono, p-disubstituted benzene). A $^1$H-NMR spectrum of Compound 2 was obtained in CDCl$_3$ with a 100 MHz NMR. The peaks were found at (ppm): δ=8.15–6.8 (m, 52H, Ar); δ=4.6–3.8 (m, 10H, CH$_2$CHCH$_2$); δ=2.9 (m, 2H, OH). An elemental analysis found the following weight percents of the elements: C, 80.98; H, 5.54; N, 7.28. which compares with the following calculated elemental weight percent for a compound with the formula C$_{76}$H$_{64}$N$_6$O$_4$: C, 81.11; H, 5.73; N, 7.47.

Preparation of Compound 3

Compound 3 was prepared according to the preparation procedure for Compound 2 except that 2,2'-bi-7-naphtol was replaced with 2.28 g (10.0 mmol) of Bisphenol A (commercially obtained from Aldrich, Milwaukee, Wis.). The reaction time was 10 hours. The reaction yielded 8.7 g (82.1%) of Compound 3 as a yellowish powder. The infrared absorption spectrum resulted in the identification of the following peaks: IR (KBr) (frequency in cm$^{-1}$): 3660–3180 (OH); 3070, 3040 (CH$_{aromatic}$); 2990, 2940, 2890 (CH$_{aliphatic}$); 830, 750, 695 (CH=CH of mono, p-disubstituted benzene). A $^1$H-NMR spectrum of Compound 3 was obtained in CDCl$_3$ with a 250 MHz NMR. The peaks were found at (ppm): δ=7.64 (s, 2H, CH=N) δ=7.50–6.93 (m, 42H, Ar); δ=6.79 (d, J=6.6 Hz, 4H of 2,2-bisphenylpropane); δ=4.39 (m, 2H, CH); δ=4.28–3.96 (m, 8H, NCH$_2$, CH$_2$O); δ=2.79 (d, J=5.5 Hz, 2H, OH); δ=1.61 (s, 3H, CH$_3$); δ=1.53 (s, 3H, CH$_3$). An elemental analysis found the following weight percents of the elements: C, 79.69; H, 6.14; N, 7.68. which compares with the following calculated elemental weight percent for a compound with the formula C$_{71}$H$_{66}$N$_6$O$_4$: C, 79.90; H, 6.23; N, 7.87.

Preparation of Compound 4

Compound 4 was prepared according to the preparation procedure for Compound 2 except that 2,2'-bi-7-naphtol was replaced with 10,10-bis(4-hydroxyphenyl)anthrone (3.78 g, 10.0 mmol, commercially obtained from Chimreaktiv, Russia). The reaction time was 10 hours. A yield of 8.3 g (68.0%) of Compound 4 was obtained as a yellowish powder. The infrared absorption spectrum resulted in the identification of the following peaks: IR (KBr) (frequency in cm$^{-1}$): 3640–3140 (OH); 3060, 3030 (CH$_{aromatic}$); 2930, 2880 (CH$_{aliphatic}$); 1665 (C=O), 825, 750, 695 (CH=CH of anthrone, mono, p-disubstituted benzene). A $^1$H-NMR spectrum of Compound 4 was obtained in CDCl$_3$ with a 250 MHz NMR. The peaks were found at (ppm): δ=8.26 (m, 2H, 1-H, 8-H of anthrone); δ=7.63 (s, 2H, CH=N); δ=7.50–6.69 (m, 50H, Ar); δ=4.38 (m, 2H, CH); δ=4.26–3.92 (m, 8H, NCH$_2$, CH$_2$O); δ=1.56 (m, 2H, OH). An elemental analysis found the following weight percents of the elements: C, 79.69; H, 5.44; N, 6.78. which compares with the following calculated elemental weight percent for a compound with the formula C$_{82}$H68N$_6$O$_5$: C, 80.90; H, 5.63; N, 6.90.

Preparation of Compound 5

Compound 5 was prepared according to the preparation procedure for Compound 2 except that 2,2'-bi-7-naphtol was replaced with 4,4'-(9-fluorenylidene)diphenol (3.5 g, 10.0 mmol, commercially obtained from Aldrich, Milwaukee, Wis.). The reaction time was 40 hours. A yield of 8.5 g (71.4%) of Compound 5 was obtained as a yellowish powder. The infrared absorption spectrum resulted in the following identification peaks: IR (film) (frequency in cm$^{-1}$): 3600–3200 (OH), 3078, 3034 (CH$_{aromatic}$); 2923, 2856 (CH$_{aliphatic}$); 824, 745, 731, 695 (CH=CH of mono, p- and o-disubstituted benzene) A $^1$H-NMR spectrum of Compound 5 was obtained in CDCl$_3$ with a 100 MHz NMR. The peaks were found at (ppm): δ=7.85–6.65 (m, 56H, Ar); δ=4.5–3.8 (m, 10H, CH$_2$CHCH$_2$); δ=2.8 (s, 2H, OH). An elemental analysis found the following weight percents of the elements: C, 81.69; H, 5.64; N, 6.98. which compares with the following calculated elemental weight percent for a compound with the formula C$_{81}$H$_{68}$N$_6$O$_4$: C, 81.79; H, 5.76; N, 7.07.

Example 4

Evaluation of Hole Mobilities for Organophotoreceptors

This example presents the evaluation of the mobility for six samples and four comparative examples.

Sample 1

Compound 2 (0.24 g) was dissolved in 1 ml of tetrahydrofuran (THF). The solution was coated on a polyester film with a conductive aluminum layer by the dip roller method. After drying for 15 min. at 80° C., a clear 5 μm thick layer was formed. The layer was positively charged by corona to surface potential U and illuminated with a 2 nanosecond nitrogen laser light pulse with a wavelength of 337 nm. Then, the hole mobility μ was determined as described in Kalade et al., "Investigation of charge carrier transfer in electrophotographic layers of chalkogenide glases," Proceeding IPCS 1994: The Physics and Chemistry of Imaging Systems, Rochester, N.Y., pp. 747–752, incorporated herein by reference. This was repeated at different U values, which correspond to different electric field strength inside the layer E. The dependence of the hole mobility μ on the electric field strength is plotted as curve 1 on FIG. 1. This dependence was approximated by the formula $$\mu = \mu_0 e^{\alpha\sqrt{E}}$$

where E is the electric field strength, $\mu_0$ is the zero field mobility and α is Pool-Frenkel parameter. The mobility characterizing parameters $\mu_0$ and α values as well as the mobility value at the 6.4×10$^5$ V/cm field strength are given in Table 1.

TABLE 1

| Sample | $\mu_0$ (cm$^2$/V · s) | $\mu$ (cm$^2$/V · s) at 6.4 · 10$^5$ V/cm | $\alpha$ | $I_p$ (eV) |
|---|---|---|---|---|
| 1 | 6.0 · 10$^{-7}$ | 7.0 · 10$^{-5}$ | 0.0060 | 5.41 |
| 2 | 8.0 · 10$^{-9}$ | 2.2 · 10$^{-7}$ | 0.0040 | — |
| 3 | 8.0 · 10$^{-7}$ | 5.4 · 10$^{-5}$ | 0.0053 | 5.39 |
| 4 | 2.0 · 10$^{-8}$ | 3.0 · 10$^{-7}$ | 0.0034 | — |
| 5 | 2.6 · 10$^{-8}$ | 7.0 · 10$^{-6}$ | 0.0070 | 5.43 |
| 6 | 5.1 · 10$^{-9}$ | 2.4 · 10$^{-7}$ | 0.0048 | — |
| 13 | 3.6 · 10$^{-6}$ | 1.3 · 10$^{-4}$ | 0.0045 | 5.45 |
| 14 | 1.4 · 10$^{-7}$ | 3.1 · 10$^{-6}$ | 0.0039 | — |
| Comparative A | 4.2 · 10$^{-8}$ | 6.0 · 10$^{-6}$ | 0.0062 | 5.35 |
| Comparative B | 1.0 · 10$^{-9}$ | 3.3 · 10$^{-7}$ | 0.0072 | — |
| Comparative C | 1.3 · 10$^{-7}$ | 1.4 · 10$^{-5}$ | 0.0058 | 5.39 |
| Comparative D | 2.9 · 10$^{-9}$ | 5.1 · 10$^{-7}$ | 0.0065 | — |

In another experiment the ionization potential of the sample $I_P$ was measured and found to be 5.41 eV by the method described in Daskeviciene et al., "Derivatives of 2,5-dimercapto-1,3,4-thiadiazole as hole transporting material", Lithuanian Journal of Physics, 2001, 41, No. 4–6, pp. 521–526, incorporated herein by reference. The ionization potential is also summarized in Table 1.

Sample 2

A mixture of 0.1 g of Compound 2 and 0.1 g of polyvinylbutyral (commercially obtained from Aldrich, cat. # 41,843-9) was dissolved in 2 ml of THF. The solution was coated on a polyester film with conductive aluminum layer by the dip roller method. After drying for 15 min. at 80° C., a clear 10 μm thick layer was formed. The hole mobility of the sample was tested as Sample 1, the results are plotted as curve 2 on FIG. 1 and presented in Table 1.

Sample 3

Sample 3 was prepared and tested according to the procedure for Sample 1 except Compound 3 was used. The test results are in Table 1.

Sample 4

Sample 4 was prepared and tested according to the procedure for Sample 2 except Compound 3 was used. The test results are in Table 1.

Sample 5

Sample 5 was prepared and tested according to the procedure for Sample 1 except Compound 4 was used. The test results are in Table 1.

Sample 6

Sample 6 was prepared and tested according to the procedure for Sample 2 except Compound 4 was used. The test results are in Table 1.

Comparative Sample A

Comparative Sample A was prepared and tested according to the procedure for Sample 1 except Compound 2 described in U.S. Pat. No. 6,214,503, incorporated herein by reference, was used. The test results are in Table 1.

Comparative Sample B

Comparative Sample B was prepared according to the procedure for Sample 2 except Compound 2 described in U.S. Pat. No. 6,214,503, incorporated herein by reference, was used. Comparative Sample B was tested according to the procedure for Sample 1. The test results are in Table 1.

Comparative Sample C

Comparative Sample C was prepared and tested according to the procedure for Sample 1 except Compound 10 described in U.S. Pat. No. 6,214,503, incorporated herein by reference, was used. The test results are in Table 1.

Comparative Sample D

Comparative Sample D was prepared according to the procedure for Sample 2 except Compound 10 described in U.S. Pat. No. 6,214,503, incorporated herein by reference, was used. Comparative Sample D was tested according to the procedure for Sample 1. The test results are in Table 1.

Example 5

Evaluation of Performance Parameters of Organophotoreceptors

This example describes the performance parameters of six samples with a charge transport compound, as described herein, and an electron transport compound.

Sample 7 was a single layer organophotoreceptor prepared as follows. First, titanyl oxyphthalocyanine dispersion was made by milling a mixture of the gamma form of titanyl oxyphthalocyanine (250 mg, ELA 7051, commercially obtained from Syntec, Berlin, Germany), polyvinylbutyral (1000 mg, S-LEC B BX-1, commercially obtained from Sekisui, Japan), THF (20 ml), a surfactant (one drop of IGEPAL® CA-720, commercially obtained from Aldrich, Milwaukee, Wis.).

This above mixture was placed into a 60 ml glass bottle together with 50 g of YTZ ceramic balls (commercially obtained from Morimura Bros.(USA), Inc., Torrance, Calif.) and shaken in a vibration mill for 1 hour to form a dispersion. A mixture of Compound 3 (400 mg), 2-(4-(1-methylethyl)-phenyl)-6-phenyl-4H-thiopyran-4-ylidene]-propanedinitril-1,1-dioxide (200 mg, commercially obtained from Syntec, Berlin, Germany as catalogue no. ST 917, herein known as ETM-1), and 1 ml of THF was poured into the dispersion (2 ml). After 1 h of gentle shaking, both Compound 3 and ETM-1 dissolved to form the coating solution. The coating solution was coated on a polyester film having a conductive aluminum layer and a 0.4 μm thick sublayer comprising methyl cellulose and methylvinylether/maleic anhydride, prepared according to U.S. Pat. No. 6,180,305. After heating for 2 h at 80° C., a 14 μm thick single layer organophotoreceptor was prepared.

The organophotoreceptor sample was charged with a scorotron to which 8.0 kV DC voltage was supplied. The scoroton charger comprises a wire that permits the transfer of a desired amount of charge to the surface of the organophotoreceptor. The grid potential was +1500 V and the charging time was 1 s. The sample was placed under a vibrating electrometer probe and the potential was measured after charging. The electrometer was connected to a C8-13 memory oscilloscope and the potential decay signal was recorded. The initial potential after charging $U_0$ and potential half decay time in the dark $t_{1/2}$ were measured. Then, the sample was charged again to the initial potential $U_0$, after which it was illuminated with 780 nm monochromatic light from a MDR-23 grating monochromator (Petersburg Optical Mechanic Amalgamation, Petersburg, Russia). Light intensity at the sample surface was 1.35·10$^{-2}$ W/m$^2$. The potential half decay time $t'_{1/2}$ at illumination was measured and photosensitivity S was calculated according to formula $$S = 1/t'_{1/2} \cdot L$$

where L is incident light intensity. The residual potential $U_R$ was measured at time $10t'_{1/2}$. The measurement results are in Table 2.

TABLE 2

| Sample | Compound | ETM | $U_0$ (V) | $t_{1/2}$ (s) | S (m²/J) | $U_R$ (V) |
|---|---|---|---|---|---|---|
| 7 | 3 | ETM-1 | 800 | 13 | 380 | 32 |
| 8 | | ETM-2 | 610 | 48 | 390 | 27 |
| 9 | 2 | ETM-1 | 740 | 26 | 370 | 30 |
| 10 | | ETM-2 | 650 | 54 | 385 | 26 |
| 11 | 4 | ETM-1 | 785 | 17 | 320 | 30 |
| 12 | | ETM-2 | 660 | 35 | 280 | 32 |

In another experiment, the organophotoreceptor was tested by repeated charging, illumination, and erasure regimes. A disk, rotating at a constant velocity, with a photoreceptor example mounted on it constitutes the main part of the cycling machine. The sample was placed in a special holder with the photoconductive layer facing down. The conductive layer of the sample was isolated from rotating disc and was connected to either an electrometer calibration voltage source, a capacitor for integration of the sample charging current, or a grounded contact. A charging, exposure and erasure module as well as five electrometer potential measurement probes were positioned under the disc at appropriate places. The disc rotation period was 1.86 s. The cycling machine performed the following operations at the time moments or intervals from the beginning of the cycle:

synchronization pulse—0;
sample charging—0–210 ms;
measurement of $U_1$ with the first probe—340 ms;
measurement of $U_2$ with the second probe—515 ms;
exposure illumination—middle at 565 ms, duration of exposure—20 ms;
measurement of $U_3$ with the third probe—615 ms, 50 ms after middle of exposure;
measurement of $U_4$ with the fourth probe—855 ms, 300 ms after middle of exposure;
erasure illumination—middle at 1140 ms, duration—100 ms;
measurement of $U_5$ with the fifth probe—1440 ms.

The current flowing through the sample was integrated into a capacitor when the sample passed under the charger. The voltage was measured by connecting the capacitor, for a certain time interval, with the computer analogue signal input. This enabled the calculation of the surface charge σ deposited on 1 cm² of the sample surface in each cycle. The data from all five electrometer probes was fed into a computer via the input board.

In some tandem color laser beam printers, the entire organophotoreceptor sample is charged and erased during printing while some areas of the organophotoreceptor that carry an image are re-charged, illuminated imagewise, developed, and erased. Therefore the electrostatic cycling was performed in the following way. The erasure lamp was on throughout the cycling. The exposure lamp was on or off in successive groups of cycles, 40 cycles in each group. Switching on and off of the exposure and erase lamps and of the charging was conducted by computer commands according to the cycling program. Exposure illumination wavelength during cycling was 780 nm, 11 ergs/cm² intensity. Erase illumination intensity was 22 ergs/cm².

The potential value $U_1$, measured with the first probe, was regarded as charging potential. The value $U_5$, measured by the probe 5 after exposure and erase illumination, was considered as residual potential $U_R$. In a printer or copying machine, development of the image may be carried out approximately 300 ms after exposure, so the potential value $U_4$, measured in 300 ms after exposure, was considered as development potential. The difference of the $U_4$ values in the cycles without exposure and with exposure was considered as electrostatic contrast $U_C$, while the value in the cycles with exposure as discharge potential. The cycling results are summarized in Table 3.

TABLE 3

| Example | Conditions | $U_1$ | $U_2$ | $U_3$ | $U_4$ | $U_5$ | $U_C$ |
|---|---|---|---|---|---|---|---|
| 7 | Beginning of cycling, cycle without exposure | 1100 | 1040 | 1005 | 940 | 53 | 870 |
| | Beginning of cycling, cycle with exposure | 1100 | 1040 | 128 | 70 | 33 | |
| | After 4500 cycles, cycle without exposure | 1060 | 980 | 940 | 880 | 53 | 808 |
| | After 4500 cycles, cycle with exposure | 1060 | 975 | 123 | 72 | 38 | |
| 8 | Beginning of cycling, cycle without exposure | 815 | 745 | 720 | 690 | 40 | 632 |
| | Beginning of cycling, cycle with exposure | 810 | 735 | 97 | 58 | 29 | |
| | After 4500 cycles, cycle without exposure | 885 | 825 | 800 | 775 | 38 | 723 |
| | After 4500 cycles, cycle with exposure | 875 | 815 | 86 | 52 | 27 | |
| 9 | Beginning of cycling, cycle without exposure | 990 | 900 | 865 | 810 | 33 | 766 |
| | Beginning of cycling, cycle with exposure | 980 | 900 | 92 | 44 | 19 | |
| | After 4500 cycles, cycle without exposure | 995 | 905 | 870 | 826 | 35 | 780 |
| | After 4500 cycles, cycle with exposure | 990 | 905 | 90 | 46 | 22 | |
| 10 | Beginning of cycling, cycle without exposure | 830 | 770 | 745 | 718 | 50 | 650 |
| | Beginning of cycling, cycle with exposure | 830 | 750 | 110 | 68 | 34 | |
| | After 4500 cycles, cycle without exposure | 840 | 775 | 755 | 720 | 50 | 650 |
| | After 4500 cycles, cycle with exposure | 835 | 770 | 105 | 70 | 35 | |
| 11 | Beginning of cycling, cycle without exposure | 980 | 910 | 880 | 845 | 55 | 770 |
| | Beginning of cycling, cycle with exposure | 990 | 920 | 160 | 75 | 31 | |
| | After 4500 cycles, cycle without exposure | 820 | 745 | 705 | 667 | 48 | 605 |
| | After 4500 cycles, cycle with exposure | 815 | 735 | 135 | 62 | 31 | |
| 12 | Beginning of cycling, cycle without exposure | 830 | 765 | 740 | 715 | 72 | 625 |
| | Beginning of cycling, cycle with exposure | 870 | 805 | 164 | 90 | 43 | |
| | After 4500 cycles, cycle without exposure | 755 | 695 | 670 | 642 | 76 | 550 |
| | After 4500 cycles, cycle with exposure | 720 | 660 | 157 | 92 | 48 | |

Figure 2:
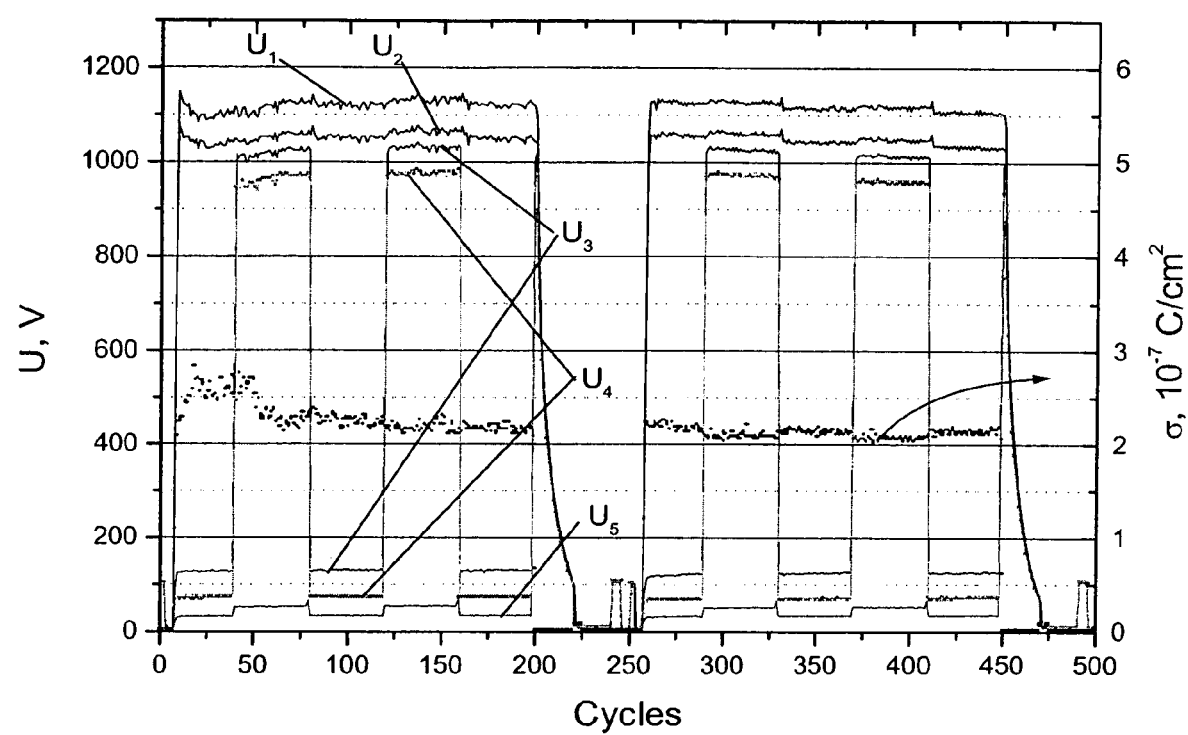
FIG. 2 is a graph representing the potential values (V) at various points in a cycling regime for a sample.

In another cycling experiment two cycling sessions were performed. The sample charging begun in the cycle 8 and ended in cycle 200. Both the imaging and erase lamps were off in the cycle 200, potential dark decay was recorded during cycles 201–220. The sample was illuminated with both lamps in the cycles 221–225, residual potential decay was recorded during the cycles 226–250. After a 10 minute break in cycling, the sample surface was illuminated at 3300–3500 lx by a fluorescent NEOLUX® EE21 lamp (commercially obtained from OSRAM GmbH, Munich, Germany) for 5 minutes. This amounted to an exposure greater than over $10^6$ lx·s. In 1 minute after cessation of illumination, the second cycling session began and everything was done exactly as in the first session. The cycling results are presented in FIG. 2 and in Table 4.

TABLE 4

| Sample | Conditions | Potentials (V) | | | | | |
|---|---|---|---|---|---|---|---|
| | | $U_1$ | $U_2$ | $U_3$ | $U_4$ | $U_5$ | $U_C$ |
| 7 | Before illumination, cycle without exposure | 1100 | 1046 | 1010 | 946 | 52 | 857 |
| | Before illumination, cycle with exposure | 1100 | 1044 | 127 | 71 | 32 | |
| | After illumination, cycle without exposure | 1120 | 1050 | 1010 | 955 | 53 | 885 |
| | After illumination, cycle with exposure | 1105 | 1035 | 125 | 70 | 35 | |
| 8 | Before illumination, cycle without exposure | 750 | 700 | 680 | 658 | 58 | 580 |
| | Before illumination, cycle with exposure | 730 | 680 | 108 | 78 | 40 | |
| | After illumination, cycle without exposure | 730 | 690 | 670 | 650 | 54 | 580 |
| | After illumination, cycle with exposure | 720 | 675 | 95 | 70 | 36 | |
| 9 | Before illumination, cycle without exposure | 990 | 905 | 865 | 815 | 34 | 770 |
| | Before illumination, cycle with exposure | 970 | 890 | 92 | 45 | 20 | |
| | After illumination, cycle without exposure | 995 | 908 | 870 | 825 | 35 | 780 |
| | After illumination, cycle with exposure | 990 | 900 | 89 | 45 | 22 | |
| 10 | Before illumination, cycle without exposure | 846 | 790 | 772 | 745 | 75 | 655 |
| | Before illumination, cycle with exposure | 845 | 780 | 150 | 95 | 49 | |
| | After illumination, cycle without exposure | 685 | 644 | 625 | 590 | 63 | 510 |
| | After illumination, cycle with exposure | 670 | 625 | 112 | 80 | 44 | |
| 11 | Before illumination, cycle without exposure | 956 | 885 | 850 | 817 | 55 | 740 |
| | Before illumination, cycle with exposure | 970 | 895 | 170 | 77 | 33 | |
| | After illumination, cycle without exposure | 900 | 830 | 790 | 760 | 52 | 690 |
| | After illumination, cycle with exposure | 900 | 825 | 152 | 70 | 31 | |
| 12 | Before illumination, cycle without exposure | 815 | 760 | 734 | 710 | 73 | 620 |
| | Before illumination, cycle with exposure | 855 | 790 | 165 | 90 | 43 | |
| | After illumination, cycle without exposure | 290 | 270 | 260 | 245 | 62 | 170 |
| | After illumination, cycle with exposure | 280 | 255 | 80 | 75 | 45 | |

Sample 8

Sample 8 was prepared and tested according to the procedure for Sample 7 except ETM-1 was replaced with ETM-2. The test results are in Tables 2–4.

Sample 9

Sample 9 was prepared and tested according to the procedure for Sample 7 except Compound 2 was used. The test results are in Tables 2–4.

Sample 10

Sample 10 was prepared and tested according to the procedure for Sample 8 except Compound 2 was used. The test results are in Tables 2–4.

Sample 11

Sample 11 was prepared and tested according to the procedure for Sample 7 except Compound 4 was used. The test results are in Tables 2–4.

Sample 12

Sample 12 was prepared and tested according to the procedure for Sample 8 except Compound 4 was used. The test results are in Tables 2–4.

Sample 13

Sample 13 was prepared and tested according to the procedure for Sample 1 except Compound 5 was used. The test results are in Tables 1.

Sample 14

Sample 14 was prepared and tested according to the procedure for Sample 2 except Compound 5 was used. The test results are in Tables 1.

The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

What is claimed is:

1. An electrophotographic imaging process comprising:
   (a) applying an electrical charge to a surface of an organophotoreceptor comprising:
      (i) a charge transport compound having the formula

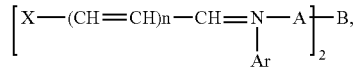

where n is an integer from 0 to 1;

X is an (N,N-disubstituted)arylamine group;

Ar is an aryl group or a heterocyclic group;

A is a first linking group with the formula —(CH$_2$)p— which can be branched or linear, where p is an integer from 3 to 20 inclusive and where one or more methylene groups can be optionally replaced by O, S, a carbonyl group, urethane, urea, an ester group, a —NR$_{21}$ group, a CHR$_{22}$ group, or a CR$_{23}$R$_{24}$ group where R$_{21}$, R$_{22}$, R$_{23}$ and R$_{24}$ are, independently, H, hydroxyl, thiol, an amine group, an alkyl group, an alkaryl group, an aryl group, or part of a ring; and B is a second linking group having the formula -Q-Z-Q'-, where Q and Q' are, independently, O, S, or NR$_1$; wherein when Q or Q' is NR$_1$ or Q=O and Q'=S, Z comprises an aryl group, and wherein when Q=Q'=S or Q=Q'=O, Z comprises a multi-ring conjugated group or —Y—W—Y'— wherein Y and Y' comprise, independently, an aryl group and W comprises a $CR_2R_3$ group; wherein $R_1$ is hydrogen or comprises an alkyl group or an aryl group; $R_2$ is a hydrogen or comprises an alkyl group, or an aryl group; and $R_3$ comprises an alkyl group or an aryl group or may form a ring structure along with the $R_2$ group;
(ii) a charge generating compound; and
(iii) an electrically conductive substrate over which said charge transport compound and said charge generating compound are located;
(b) imagewise exposing said surface of said organophotoreceptor to radiation to dissipate charge in selected areas and thereby form a pattern of charged and uncharged areas on said surface;
(c) contacting said surface with a toner to create a toned image; and (d) transferring said toned image to a substrate.

2. An electrophotographic imaging process according to claim 1 wherein the toner is a liquid toner comprising a dispersion of colorant particles in an organic liquid.

3. An electrophotographic imaging process according to claim 1 wherein said organophotoreceptor further comprises an electron transport compound.

* * * * *